US009814766B2

(12) United States Patent
Fischer et al.

(10) Patent No.: US 9,814,766 B2
(45) Date of Patent: Nov. 14, 2017

(54) MULTIMODAL ANTIMICROBIAL THERAPY

(71) Applicant: Longhorn Vaccines and Diagnostics, LLC, Bethesda, MD (US)

(72) Inventors: Gerald W. Fischer, Bethesda, MD (US); Richard F. Schuman, Boyds, MD (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 0 days.

(21) Appl. No.: 14/584,110

(22) Filed: Dec. 29, 2014

(65) Prior Publication Data

US 2015/0182606 A1    Jul. 2, 2015

Related U.S. Application Data

(60) Provisional application No. 61/921,442, filed on Dec. 28, 2013.

(51) Int. Cl.
| | |
|---|---|
| *A61K 38/48* | (2006.01) |
| *C12N 9/64* | (2006.01) |
| *A61L 31/16* | (2006.01) |
| *A61K 9/50* | (2006.01) |
| *A61K 9/16* | (2006.01) |
| *A61L 29/16* | (2006.01) |
| *A61K 45/06* | (2006.01) |
| *A61K 9/00* | (2006.01) |

(52) U.S. Cl.
CPC ........ *A61K 38/4886* (2013.01); *A61K 9/0073* (2013.01); *A61K 9/16* (2013.01); *A61K 9/50* (2013.01); *A61K 45/06* (2013.01); *A61L 29/16* (2013.01); *A61L 31/16* (2013.01); *C12N 9/6489* (2013.01); *A61L 2300/254* (2013.01); *A61L 2300/404* (2013.01); *A61L 2300/45* (2013.01); *C12Y 304/24075* (2013.01)

(58) Field of Classification Search
None
See application file for complete search history.

(56) References Cited

U.S. PATENT DOCUMENTS

| | | | |
|---|---|---|---|
| 3,278,378 A | 10/1966 | Schindler et al. | |
| 4,931,390 A | 6/1990 | Recsei | |
| 5,270,176 A | 12/1993 | Dorschug et al. | |
| 5,571,511 A | 11/1996 | Fischer | |
| 5,955,074 A | 9/1999 | Fischer | |
| 6,315,996 B1 | 11/2001 | O'Callaghan | |
| 6,610,293 B1 | 8/2003 | Fischer et al. | |
| 6,632,432 B1 | 10/2003 | Fischer | |
| 6,897,041 B1 | 5/2005 | Khatri et al. | |
| 6,939,543 B2 | 9/2005 | Fischer et al. | |
| 7,014,850 B2* | 3/2006 | Fischetti ................ | C12N 9/503 424/93.6 |
| 7,279,162 B1 | 10/2007 | Fischer | |
| 7,452,533 B2 | 11/2008 | Walsh et al. | |
| 8,241,901 B2 | 8/2012 | Huang et al. | |
| 8,568,714 B2 | 10/2013 | Donovan et al. | |
| 2007/0202051 A1* | 8/2007 | Schuschnig .......... | A61K 9/0043 424/45 |
| 2007/0212340 A1* | 9/2007 | Fischetti .............. | A61K 38/162 424/94.2 |
| 2007/0292404 A1* | 12/2007 | Walsh ............... | A61K 47/48215 424/94.3 |

FOREIGN PATENT DOCUMENTS

WO    WO 2008/105826    9/2008

OTHER PUBLICATIONS

PCT Search and Patentability Report for PCT/US2014/72506, dated Mar. 20, 2015.
Canadian Office action dated Apr. 21, 2017.
EPO Search Report for Application No. 14874375, dated Jun. 8, 2017.
Thallinger, B, et al. "Antimicrobial enzymes: An emerging strategy to fight microbes and microbial biofilms," Biotechnology Journal 2013 Wiley-VCH Verlag Deu, vol. 8, No. 1, Jan. 2013, pp. 97-109.

* cited by examiner

*Primary Examiner* — Melissa Fisher
(74) *Attorney, Agent, or Firm* — Remenick PLLC

(57) ABSTRACT

The present invention is directed to compositions and methods for preventing and/or treating diseases and disorders of patients caused by non-Staphylococcal microorganisms. In particular, compositions and methods contain lysostaphin, altered forms of lysostaphin as compared to wild-type, and synergistic combinations of lysostaphin plus additional conventional treatments such as other enzyme, antibiotic and/or antibody treatment. The invention is also directed to detecting and identifying altered forms of lysostaphin that possess increased efficacy against infections as compared to wild-type lysostaphin, and forms that generate a minimal or no immune response in a patient. The invention is also directed to method of manufacturing lysostaphin and altered forms of lysostaphin, and compositions that direct the lysostaphin to the site of the infection such as aerosolized nanoparticles.

26 Claims, 5 Drawing Sheets

MULTIMODAL ANTIMICROBIAL THERAPY

REFERENCE TO RELATED APPLICATIONS

This application claims priority to U.S. Provisional Application No. 61/921,442 of the same title and filed Dec. 28, 2013, the entirety of which is hereby incorporated by reference.

BACKGROUND

1. Field of the Invention

The present invention is directed to compositions and methods for treating diseases and disorders of patients and, in particular, compositions, uses of the composition and methods for treating infections of patients with lysostaphin and synergistic combinations of lysostaphin and conventional treatments such as antibiotics, antibodies or other enzymes. The invention is also directed to methods for the treatment of infections, and in particular non-Staphylococcal infections, with lysostaphin and/or altered forms of lysostaphin that possess increased efficacy against infections as compared to wild-type lysostaphin. The altered forms preferably generate a minimal or no immune response in a patient as compared with wild-type lysostaphin.

2. Description of the Background

*Staphylococcus aureus* (SA) is a major cause of severe infections of animals and people. In humans, a skin infection may rapidly progress from a mild local infection or wound to sepsis, multi-organ system failure, shock and death within hours. Surgical patients, diabetics and premature infants are also highly susceptible to infection and individuals with catheters, artificial valves and other foreign bodies may develop colonization of these devices that are very difficult treat. Over the last several years, SA has become resistant to many key antibiotics including the first line penicillins (e.g. multi-drug resistant *Staphylococcus aureus* or generally MRSA). These organisms have spread around the world and MRSA is a major cause of both community and hospital acquired infections.

Lysostaphin is an effective agent for treating SA infections in that it attacks both actively growing and quiescent Staphylococcal bacterial cells. This enzyme cleaves the pentaglycine bridge in the cell wall of SA. The cell walls of other microbes such as *M. tuberculosis* (MTB) are very different from SA and many antibiotics that are effective for treating SA infections do not work well for treating MTB. The cell wall of MTB is about 60% lipid and can evade the immune system and render many common antibiotics ineffective. MTB is also difficult to treat because it replicates only about every 20 hours and can even become dormant and replicate little if at all. These characteristics and the rapid rise of strains that are resistant to current anti-MTB antibiotics make effective therapy increasingly difficult.

There is a need for new approaches for treating MTB and other microbial infections.

SUMMARY OF THE INVENTION

The present invention overcomes the problems and disadvantages associated with current strategies and designs and provide new tools and methods for treating infections that are caused by a microbe other than *Staphylococcus*.

One embodiment of the invention is directed to compositions and in particular pharmaceutical compositions for administration to a patient in need thereof comprising lysostaphin wherein the patient has an infection or is at risk of infection by a microorganism other than *Staphylococcus*. Preferably the lysostaphin is wild-type lysostaphin isolated from *Staphylococcus staphylolyticus* or *Staphylococcus staphylolyticus* that is cultured from selective media or from another organism or cell type (e.g., *E. coli*, insect cells, mammalian cells transfected with lysostaphin sequences). Preferably the selective media comprises glucose and also preferably the lysostaphin is recombinant lysostaphin isolated from *E. coli* bacteria or another cell type. Preferably the lysostaphin has one or more amino acids or one or more amino acid modifications that differ from wild-type lysostaphin and the lysostaphin has a greater efficacy against MTB or another non-SA bacterial infection as compared to wild-type lysostaphin. Also preferably the lysostaphin is sufficient to clear and/or kill the non-SA microorganisms when administered to the patients is at risk of acquiring an MTB or other microbial infection.

Another embodiment of the invention is directed to lysostaphin therapy for prophylaxis or treatment of active or suspected infections. Preferably lysostaphin therapy further comprises a secondary therapy for the patient in need thereof that is synergistic with the lysostaphin. Synergistic therapies include use of agents such as, for example, other enzymes, chemicals, peptides, cell wall and/or non-cell wall active agents, and/or antibodies that are effective against the microbe, such as anti-MTB medications. Preferred agents include one or more of the chemical forms and derivatives of penicillin, antibiotics such as, for example nicin, bacteriocins, amoxicillin, augmentin, polymyxins, isoniazid, rifampin, ethambutol, Pyrazinamide, aminoglycosides, colistins, cycloserine, autolysin, bacitracin, cephalosporin, vancomycin, and/or beta lactam. Also preferably, the lysostaphin is synergistic in combination with agents that are cell wall active agents. Preferably the antibiotics are administered as one or more doses to the patient in need thereof at an effective dose that is lower than the recommended dose for administration of the antibiotic alone and the composition further comprises a pharmaceutically acceptable carrier such as, for example, one or more of oil, fatty acids, lipids, polymers, carbohydrates, gelatin, solvents, saccharides, buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents or an immunological inert substance, a carrier designated as generally recognized as safe (GRAS), or a combination thereof.

Another embodiment of the invention is directed to methods for treating infections, other than *Staphylococcus* infections, comprising administering to a patient in need thereof a composition comprising lysostaphin preferably at levels effective to kill the infectious organism. Preferably the composition is administered orally, aerosolized (e.g. as nanoparticles to the lungs), encapsulated, prepared as slow-release, injected including intravenously or subcutaneously injected, and/or injected to a site of infection. Also preferably the composition is coated onto an object to be inserted into the body of the patient wherein the object is inserted into an area of the body that is infected and/or sequestered from the patient's immune system. Preferably the composition has reduced negative effects or increased positive effects for the patient as compared with conventional therapy. Preferably the reduced negative effects include one or more of reduced toxicity and reduced immunogenicity and the enhanced positive effects include one or more of increased efficacy and enhanced microbial clearance from a patient system.

Other embodiments and advantages of the invention are set forth in part in the description, which follows, and in part, may be obvious from this description, or may be learned from the practice of the invention.

DESCRIPTION OF THE INVENTION

Figure 1:
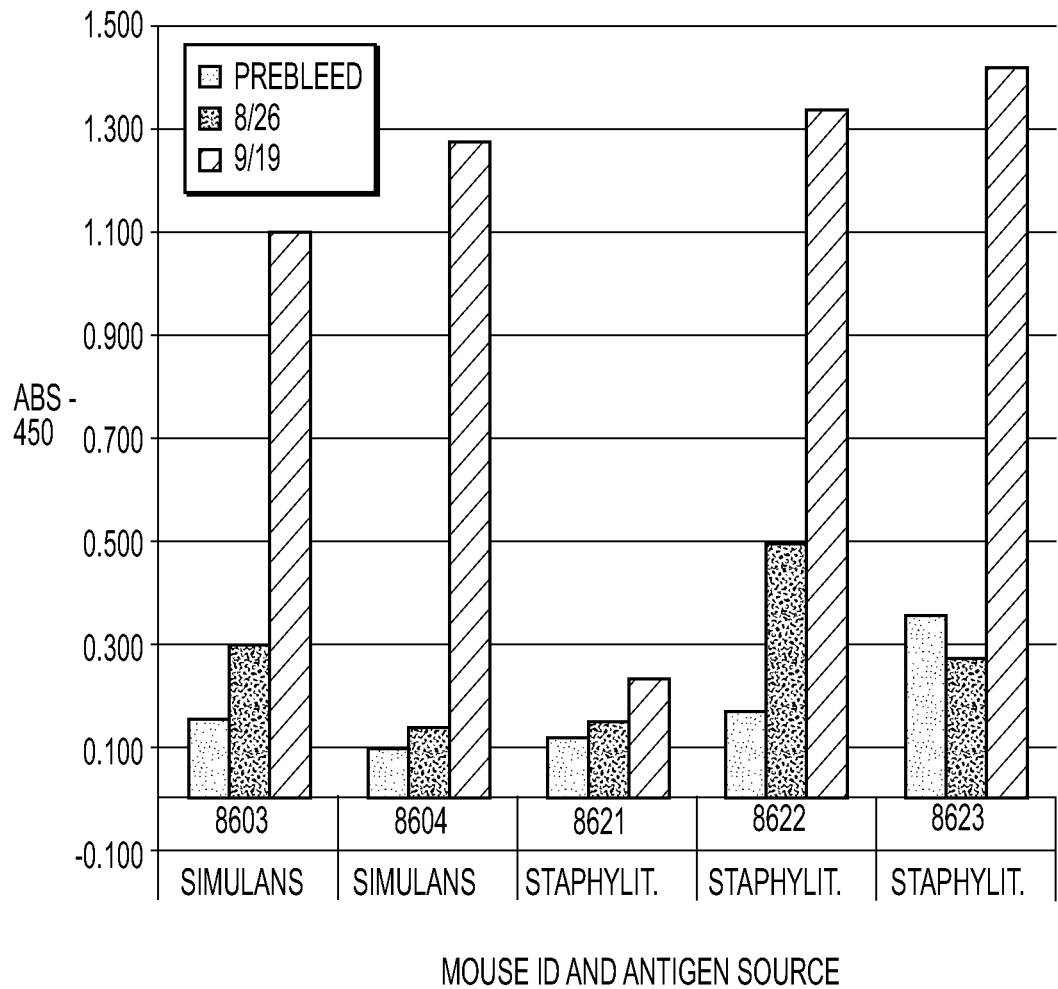
FIG. 1 Antibody values of mouse sera binding to lysostaphin-coated plates.

Lysostaphin is a well-know bacteriocin secreted by cells of staphylococcal bacteria and isolated from S. simulans. The production of lysostaphin is well known and the enzyme is commercially available (U.S. Pat. No. 3,278,378). The lysostaphin gene encodes a preproenzyme of Mr 42,000. The $NH_2$-terminal sequence of the preproenzyme is composed of a signal peptide followed by seven tandem repeats of a 13-amino acid sequence. Conversion of pro-lysostaphin to the mature enzyme occurs extracellularly in cultures of S. simulans and involves removal of the $NH_2$-terminal portion of the proenzyme that contains the tandem repeats. The high degree of homology of the repeated regions would suggest that the repeats arose from duplication of a 39-base-pair sequence of DNA. Recsei et al, Proc Natl Acad Sci USA. March; 84(5):1127-31 (1987).

Lysostaphin is a 27 kD glycylglycine endopeptidase that functions in cell killing by cleaving the pentaglycine bridge of bacterial cell walls. As such, lysostaphin is a potent anti-Staphylococcal enzyme. Lysostaphin therapy for experimental endocarditis and sepsis utilized large IV doses; standard anti-SA antibiotics can be added as well (U.S. Pat. No. 8,198,231). For treating serious SA infections (such as endocarditis with bacteremia) in animal models, typical doses of lysostaphin used were from 10-50 mg/kg and for up to 6 weeks. Treatment was focused on direct lysis of SA cells by lysostaphin, and thus, similar regimens have been extrapolated for treating severe SA infections in humans. These high intravenous doses may have deleterious effects related to infusing a protein/enzyme into the blood stream such as inducing antibodies, kidney disease and/or vasculitis.

It has been surprisingly discovered that microbes other than Staphylococcus can be effectively treated with compositions containing lysostaphin. Microbes other than SA can be lysed, or destroyed with compositions containing lysostaphin. A principal mechanism of action is believed to be the enzymatic function of lysostaphin which is cleaving of the pentaglycine bridge of bacterial cell walls. Thus, enzymes of similar function (lysostaphin is a glycyl-glycine endopeptidase) can be effective against cell walls of similar chemical structure (e.g. gram positive bacteria that infect intracellularly such as Mycobacteria and, in particular, M. tuberculosis {MTB}). Lysostaphin compositions can be delivered in a manner that is preferably effective at a dosage used to treat SA infections or can be effective at reduced dosage that minimize side effects due the lysostaphin itself and/or in combination with other treatments including synergistic strategies. These include, but are not limited to aerosol delivery and/or sequential pulses of lysostaphin to disrupt cell walls and promote immune clearance, while controlling the blood lysostaphin level. Preferably antibiotics are given at selected intervals as well to synergize with the local or systemic levels of lysostaphin.

The composition and methods of the invention are useful for treating and/or preventing infections of a number of pathogens including, but not limited to unusual and slow growing microbes such as mycobacteria and nocardia, intracellular bacteria, gram positive bacteria, gram positive bacteria that are intracellular including, for example, Mycobacterium (e.g., M. tuberculosis {active and/or latent}, Nocardia, and Actinomyces. The compositions and methods of the invention are useful to treat microbial infection that is caused by an organism that is generally susceptible to an antibiotic irrespective of the acquisition or development of resistance to the antibiotic.

Further, lysostaphin therapy can be synergistically combined with other effective treatments for infections caused by non-SA microorganisms. This synergism, as compared to conventional therapy, allows for lower dosages of either or both medications and, therefore, evokes fewer or no side effects due to the particular medication and further potentially allows for a lower cost of treatment. The benefits of reduced dosing include, but are not limited to a potentially reduced impact to the immune system, kidneys, livers, heart, lungs and other major organs and systems of a body. Blood pressure is less affected (which may otherwise increase or decrease), clearance of medication from the patient's system is accelerated, immune system response (as in allergic response and/or inflammation) may be reduced or eliminated, as well as all known side effects of a medication such as, for example, anemia, hemophilia and other bleeding disorders, platelet deficiency and other clotting disorders, risks of blood-derived and other cancers, and all risks and side effects of the particular therapy.

It was also surprisingly discovered that synergy of other active agents with lysostaphin could be better achieved with low doses of lysostaphin. Although higher doses of lysostaphin would result in greater overall percent killing of microorganisms, with lower doses a synergy could be observed with a secondary active agent. Preferred secondary active agents include but are not limited to agents that are active against cell wall construction, cell wall lysis, replication, transcription, translation, polymerases and other specific enzymes, and other major functions associated with bacteriostatic and/or bactericidal activity.

One embodiment of the invention is directed to methods for treating infections other than Staphylococcal infections with lysostaphin to prevent or to treat infection such as, preferably, infections by Mycobacterium such as M. Tuberculosis. Preferably these one or more doses contain additional antibiotics or antibacterial compounds (bacteriostatic or bactericidal), or possibly antibodies or other compounds to generate or enhance the patient's immune response to an infection. Also preferably, the compositions contain a pharmaceutically acceptable carrier that is a recognized and approved by an appropriate authority (e.g., U.S. Food and Drug Administration, European Medicine's Agency).

Composition of the invention may also contain or be administered with a secondary therapy, such as, for example, bacteriostatic or bactericidal therapy, antibody therapy (e.g., anti-microbial antibodies such as monoclonal or polyclonal antibodies or antibody fragments), and/or antibiotic therapy (e.g. one or more of antibiotics such as for example nicin), bacteriocins, vancomycin, teicoplanin, telavancin, clindamycin, lincomycin, linezolid, rifampin, polymyxins (e.g., Polymixin B and C), neomycin, cefalexin, ceftaroline fosamil, ceftobiprole), treatment with another medication against the infection, and especially slow-growing bacteria such as MTB infections, or a combination of these secondary treatments. The combination of lysostaphin with a secondary therapy creates a synergy that improves treatment outcome or allows for a reduction in amount, dosage and/or concentration as compared to conventional dosing of the secondary therapy alone. Preferred classes of antibiotics that can be combined with lysostaphin therapy for treatment of patients are listed in Table 1.

TABLE 1

Useful Classes of Antibiotics

| | | |
|---|---|---|
| Aminoglycosides | Lincosamides | Polypeptides |
| Ansamycins | Lipopeptide | Quinolones |
| Bacteriosins | Lantbiotics | Rifampin |
| Carbacephem | Macrolides | Sulfonamides |
| Carbapenems | Nitrofurans | Tetracyclines |
| Cephalosporins | Oxazolidonones | Anti-Mycobacterial compounds |
| Glycopeptides | Penicillins | |

Medications listed in Table 1 are preferably administered at a reduced concentration, as compared to conventional and individually recommended dosages, when administered in combination with lysostaphin therapy. The combinations produce surprising synergistic effects on the host which is preferably a human patient or non-human patient (e.g., preferably mouse or other mammal), often clearing an infection with little or no ill effects to the patient as can be seen with higher doses of lysostaphin and/or higher doses of the one or more antibiotics alone.

Another embodiment of the invention is directed to methods for administering to a patient in need thereof, a composition containing lysostaphin, synergistic compounds with lysostaphin and/or preferred forms of lysostaphin that are altered as compared to wild type or conventional lysostaphin. Preferably, the antimicrobial activity of the composition (e.g. the lysostaphin and/or the lysostaphin plus the synergistic compounds of the composition) has an activity of 50% or greater, more preferably 70% or greater, more preferably 80% or greater, more preferably 90% or greater, more preferably 95% or greater, and more preferably 99% or greater. Preferably the ratio of active to inactive forms of lysostaphin is two or greater, three or greater, five or greater, seven or greater, or ten or greater. Maximization of activity allows for the administration of minimal dosages and thereby reduces the risk of immunogenicity.

Preferably these one or more doses are administered simultaneously or over a course of time (before or after administration of lysostaphin) with the secondary therapy such as, for example, cell wall active agents, polymerase inhibitors, antibiotics, antimicrobials, antibacterial chemicals and chemical compounds, and other enzymes (e.g. chemical forms and derivatives of penicillin, amoxicillin, augmentin, bacteriocins, polymyxins, colistins, cycloserine, autolysin, bacitracin, cephalosporin, antibiotics, rifampin, vancomycin, beta lactam), or possibly antibodies or other compounds to generate or enhance an immune response to the infection. Preferably the antibiotic functions synergistically with the lysostaphin of the invention to provide an efficient and effective preventative or treatment of an infection whether active or slow-growing microbes. Lysostaphin compositions may be administered to treat infections that have sensitivity or resistance to certain antibiotics, such as for example antibiotic resistant MTB. Treating infections that are sensitive to antibiotics prevents the development and/or the rise of antibiotic resistant forms. Also preferably, administration of antibiotics with lysostaphin may be alternated and/or staggered to prevent and/or reduce the risk of developing resistance to the antibiotic or to the lysostaphin molecule.

The compositions of the invention may be administered orally, parenterally (e.g., intravenously), topically, transdermally, by intramuscular injection, or injection to the site of infection or by intraperitoneal injection, or the like, although oral administration is generally preferred. Administration can be continuous (e.g., drip, infusion, delayed or gradual release), or site specific, such as to sites of a patient that are sequestered from the patient's immune system (e.g., areas of the central nervous system {CNS}, areas behind the blood-brain barrier, peripheral nerve canals, optical cavities and optical nerves), and to areas of that body the receive only reduced or limited immunological activity (e.g., areas with limited blood flow). Administration may also be by aerosol formulations, encapsulation, liposomal formulations and may include the coating of objects that are placed fully or partially into the patient, such as the coating of catheters, drainage tubes (e.g., for CNS drainage). Methods to coat medical objects and compositions formulated to maintain coatings to objects are well-known to those skilled in the art (Boston Scientific Corporation of Natick, Mass. and see U.S. Pat. Nos. 8,034,119 and 8,597,673).

The composition may also comprise lysostaphin coupled with an antibody that directs or drives the antibody to a specific site, such as for example, the site of an active infection within the patient. Preferably the antibody and the lysostaphin are covalently coupled and also preferably, the antibody and the lysostaphin may be directed to a site that contains enzymes that cleave the coupling releasing the lysostaphin intact or functionally active. The antibody may have activity against the infection (e.g., an anti-microbial {non-Staph} antibody such as MTB) or have another beneficial effect to the patient, or the antibody is used solely to direct or target the placement and/or activity of the lysostaphin, such as, for example, to a specific organ, tissue, cell surface, or site within the body of the patient.

The amount of lysostaphin in compositions of the invention administered as one or more doses to patients is dependent on, for example, the weight of the patient and the mode of administration. When administered to specific sites, such as for example, by injection to a site of infection, injection to a confined region or the patient's body, or aerosolization to the lungs, dosages can be substantially reduced from a total weight-based amount. Generally, the dosage will be in the range of preferably between about 1 μg to 10.0 mg per kg of patient body weight, more preferably between about 10 μg to 7.0 mg per kg of patient body weight, more preferably between about 50 μg to 5.0 mg per kg of patient body weight, and more preferably between about 100 μg to 3.0 mg per kg of patient body weight. Dosages not based on patient total weight preferably provide an effective serum (or plasma) or tissue level of lysostaphin at from about 0.001 μg/ml to about 1.0 mg/ml, also preferably from about 0.005 μg/ml to about 500 μg/ml, also preferably from about 0.01 μg/ml to about 100 μg/ml, also preferably from about 0.02 μg/ml to about 50 μg/ml, also preferably from about 1.0 μg/ml to about 10 μg/ml and also preferable combinations therein. Dosages may be administered as a single bolus, every 8 hours, every 12 hours (bid), daily (qd), every other day (qod), or the frequency of administration empirically determined by one skilled in the art as appropriate to treat the infection. Administration is typically sufficient for 5 days, for 7 days, for 10 days, for 14 days, or can be for shorter or longer periods of time as determined by one skilled in the art.

Doses may also be as international units. One international unit (IU) is about 3.1 µg and will reduce the turbidity (A620) of a suspension of *S. aureus* cells from 0.250 to 0.125 in 10 minutes at pH 7.5 at 37° C. in a 6.0 ml reaction mixture.

Preferably the lysostaphin compositions of the invention are aerosolized to a degree that is effective, for example, when treating infections of the lungs. Preferably compositions are aerosolized to nanoparticles or particles of about 1-3 microns that are able to reach deep into lung tissue. Such small particles are also taken up by macrophages and delivered to the site of the infection. The amount of lysostaphin administered is dependent on, for example, the weight of the patient, the severity of infection, and/or the mode of administration.

Also preferably, the lysostaphin compositions of the invention may be encapsulated such as, for example, as liposomes, or as nanoparticles, or prepared as emulsions or microspheres, or with biodegradable coating for slow-release and timed-release formulations. Biodegradable coatings are preferably polymers or co-polymers such as, for example, carbohydrates, lipids, fatty acids, peptides, proteins, nucleic acids and combinations thereof.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The lysostaphin may be encapsulated for immediate or slow release (e.g. carbohydrate or sugar coatings), aerosolized to the site of the infection as, for example, nanoparticles. The compositions may include, as noted above, an effective amount of lysostaphin in combination with a pharmaceutically acceptable carrier and, in addition, may include other medicinal agents, pharmaceutical agents, carriers, adjuvants, diluents, and the like. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known or apparent to those skilled in this art (e.g., see Remington's Pharmaceutical Sciences. 15th Edition. Edited under the direction of Arthur Osol and John E. Hoover. Mack Publishing Co., which is hereby incorporated by reference).

For oral administration, fine powders or granules may contain diluting, dispersing, and/or surface active agents, and may be presented in water or in a syrup, in capsules or sachets in the dry state, or in a non-aqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained (e.g., U.S. Pat. No. 3,710,795, which is hereby incorporated by reference).

Another embodiment of the invention is directed to methods for the production of altered forms of lysostaphin that show greater efficacy against the non-Staphylococcal infection. Production methods preferably include isolation of lysostaphin from cultures of bacteria containing a selective grown medium. Preferred growth media ingredients include, but are not limited to serum, carbohydrate (e.g., glucose, sucrose, fructose), one or more bacterial cell growth factors, one or more vitamins and/or one or more essential or non-essential amino acids. Growth of bacterial strains is preferable at optimum proliferation temperatures (typically 37° C.) and more preferably at temperatures reduced from optimal. Also preferred is growth with selective pressure to promote a desired phenotypic characteristic. By way of a non-limiting example, bio variant *Staphylococcus* simulans (subsp. *Staphylolyticus*) is preferably grown at about 37° C., more preferably about 32° C. or less, more preferably about 30° C. or less, and more preferably about 28° C. or less. Increased cultivations temperatures as well as variation in temperature can also generate expression of altered forms of lysostaphin.

The form (e.g., 3D structure, immunogenicity, nucleic acid and/or amino acid sequence, post-translation modification) and activity of lysostaphin can be altered by the methods of production. For example, lysostaphin activity, function and/or immunogenicity can be increased or decreased as compared to wild-type (wt.) forms by adjusting, for example, the pH, the temperature, or the composition of the growth media (e.g., glucose level, amino acid choice and composition, serum type and/or percentage, etc.) of the culture. Isolation and/or purification of lysostaphin from cultures grown with selected ingredients and/or at reduced temperatures generates variants that have one or more altered amino acid sequences, one or more altered chemical modifications, and/or altered folding or 3-D configurations. These altered forms of lysostaphin show a reduced capacity to generate an immune response in patients upon injection and/or provide increased efficacy of the lysostaphin against infection. Alterations of the sequence can be created with recombinant techniques as well. Alterations of chemical modifications can be directed by the particular cultures in which the enzyme is cultivated such as, for example, cell cultures of *E. coli*, *Staphylococcus* simulans (*staphylolyticus*), *Lactococcus lactis*, *Lactobacillis fermentum*, or *Lactobacillus rhamnosus*. Altered form of lysostaphin are isolated and purified from these cultures as the same manner as wild-type or natural lysostaphin.

Another embodiment of the invention is directed to compositions comprising altered forms of lysostaphin. The preferred amino acid sequence is of wild-type or normal lysostaphin derived from *Staphylococcus* simulans (SubSp. *staphylolyticus*). Altered forms of lysostaphin of the invention may preferably contain one or more amino acid substitutions, amino acid modifications, one or more amino acid deletions and/or one or more amino acid additions to the sequence. Altered forms possess an altered 3-D structure, configuration and/or folding to the protein molecule thereby providing certain advantages. For example, altered forms of lysostaphin preferable have a greater efficacy and an increased potency against infection and/or faster acting function. Also preferable, these altered forms are minimally or completely non-reactive to the patient's immune system (decreased or no immunogenicity) causing the generation of minimal or no humoral, cellular or inflammatory response. As a direct result, treatment of patients with an altered form of lysostaphin of the invention would produce reduced side effects as compared to previously known lysostaphin treatment, toxicity may be reduced and clearance enhanced. The burden to a patient's organ system such as the liver or kidneys, would be reduced which may allow for increased dosages and even greater efficacy. Altered lysostaphin therapy can also be combined with other therapies such as, for example, antibody and/or antibiotic therapy as described herein.

The following examples illustrate embodiments of the invention, but should not be viewed as limiting the scope of the invention.

EXAMPLES

Example 1

In this assay, ethanol-killed MTB were added to duplicate wells at dilutions of 1:2, 1:4 and 1:8 in PBS. One well of each pair received 100 µl of PBS and the other well received 100 µl of recombinant lysostaphin at 750 µg/ml (final concentration=375 µg/ml of recombinant simulans lysostaphin produced in E. coli). The % T was determined after 3 minutes, 10 minutes and 20 minutes.

TABLE 2

Treatment of EtOH-Fixed TB with 375 µg/ml of Recombinant Lysostaphin

| Bacterial Dilution | % T at 3 min | | % T at 10 min | | % T at 20 min | |
|---|---|---|---|---|---|---|
| | PBS | 375 µg/ml | PBS | 375 µg/ml | PBS | 375 µg/ml |
| 1:2 | 60.695 | 86.268 | 41.02 | 91.59 | 49.917 | 92.587 |
| 1:4 | 68.715 | 95.356 | 57.83 | 77.33 | 60.249 | 92.651 |
| 1:8 | 79.552 | 97.308 | 64.31 | 98.03 | 78.046 | 98.186 |

In all cases (i.e., at all dilutions of bacteria) the % T increased in the groups receiving lysostaphin, indicating that the enzyme was disrupting the bacterial cell wall. This demonstrates that slow growing, dormant or even dead MTB can be lysed and destroyed by lysostaphin. The MTB cell wall glycines are positioned such that despite the large cell wall mycolic acid content, lysostaphin can penetrate and cleave the glycine structures. These data demonstrate a new approach for treating slow growing or dormant bacteria that are otherwise hard to kill Combined therapy (administered through one or more routes) with antimicrobial chemicals, peptides antibiotics or antibodies would increase the rate of killing of MTB or prevent resurgent growth of remaining viable bacteria and allow decreased concentrations of the anti-microbial agents. The treatment is delivered to the site of infection, such as the lung, to allow local treatment with lower quantity of systemic lysostaphin. By encapsulating the composition administered enzymes and/or antimicrobials are created to be slow or timed released formulation. For lung delivery, compositions are aerosolized to about 3 microns in particle size or less (e.g. nanoparticles) and administered orally or injected directly to the lungs.

Example 2

Two lysostaphin products are injected into mice (one produced in S. Simulans, subspecies S. staphylolyticus {natural}, and one produced in E. coli designated S. simulans {recombinant}). As lysostaphin is an immunogenic protein, when injected (into people or animals) antibodies are generated that may cause side effects after previous exposure. Anti-lysostaphin antibodies are produced in the serum by both products. Despite the fact that both products induced similar anti-lysostaphin antibodies, the antibodies induced by both products had markedly higher binding to non-recombinant lysostaphin compared to recombinant lysostaphin (see FIG. 1). One animal in the non-recombinant lyso-group produced almost no antibody response. Surprisingly, these data demonstrate that the method of production can provide a lysostaphin molecule that has increased binding to anti-lysostaphin antibodies. The recombinant lysostaphin is less reactogenic and more potent than conventionally produced lysostaphin. Thus, this data shows that production methods can specifically alter immunogenic properties and enhance potency to provide effective therapy at ultra-low doses and minimize side effects.

Example 3

Assay of mouse sera on plates coated with lysostaphin from simulans expressed as recombinant in E. coli and coated with natural lysostaphin from S. staphylolyticus. Mice received a primary immunization (subcutaneous) with 10 µg recombinant lysostaphin from E. coli (Sigma-Aldrich) (animal numbers 8603, 8604) or 10 µg of natural lysostaphin from S. staphylolyticus (Sigma-Aldrich) (animal numbers 8621-8623). Primary immunization was administered and boosted about three weeks later. No adjuvant was used for the immunizations.

Figure 2:
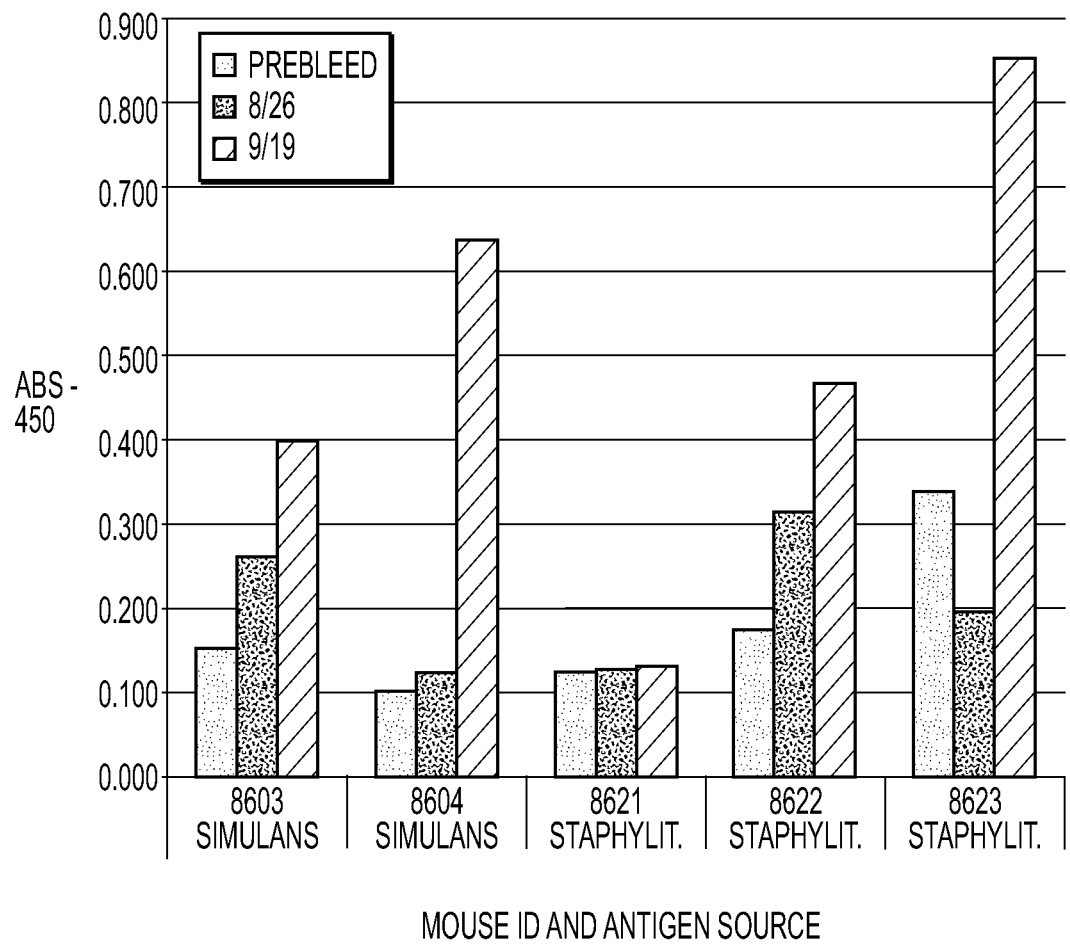
FIG. 2 Antibody values of mouse sera binding to lysostaphin-coated plates.
Figure 3:
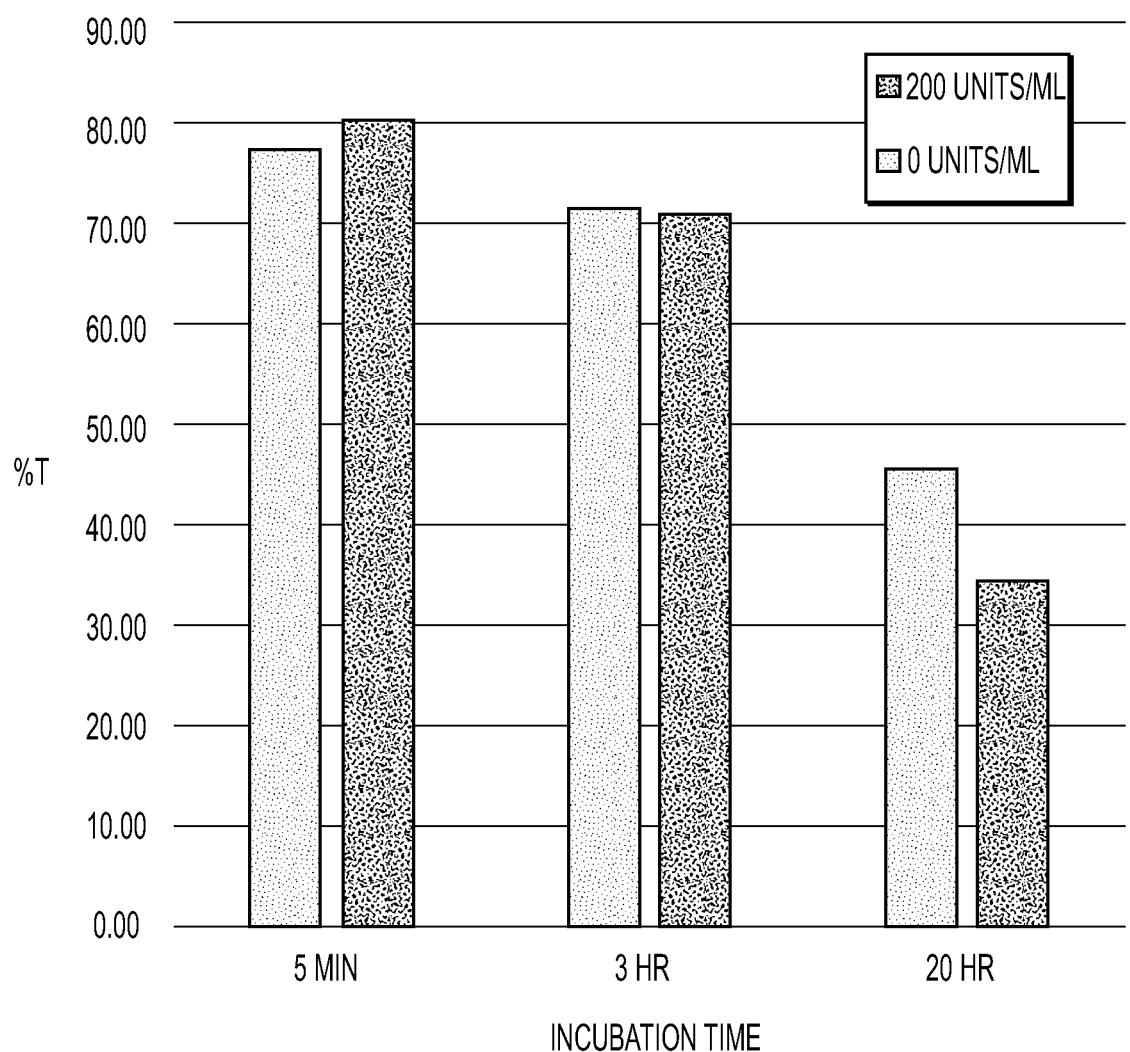
FIG. 3 Effect of Lysostaphin on growth of M. smegmatis.
Figure 4:
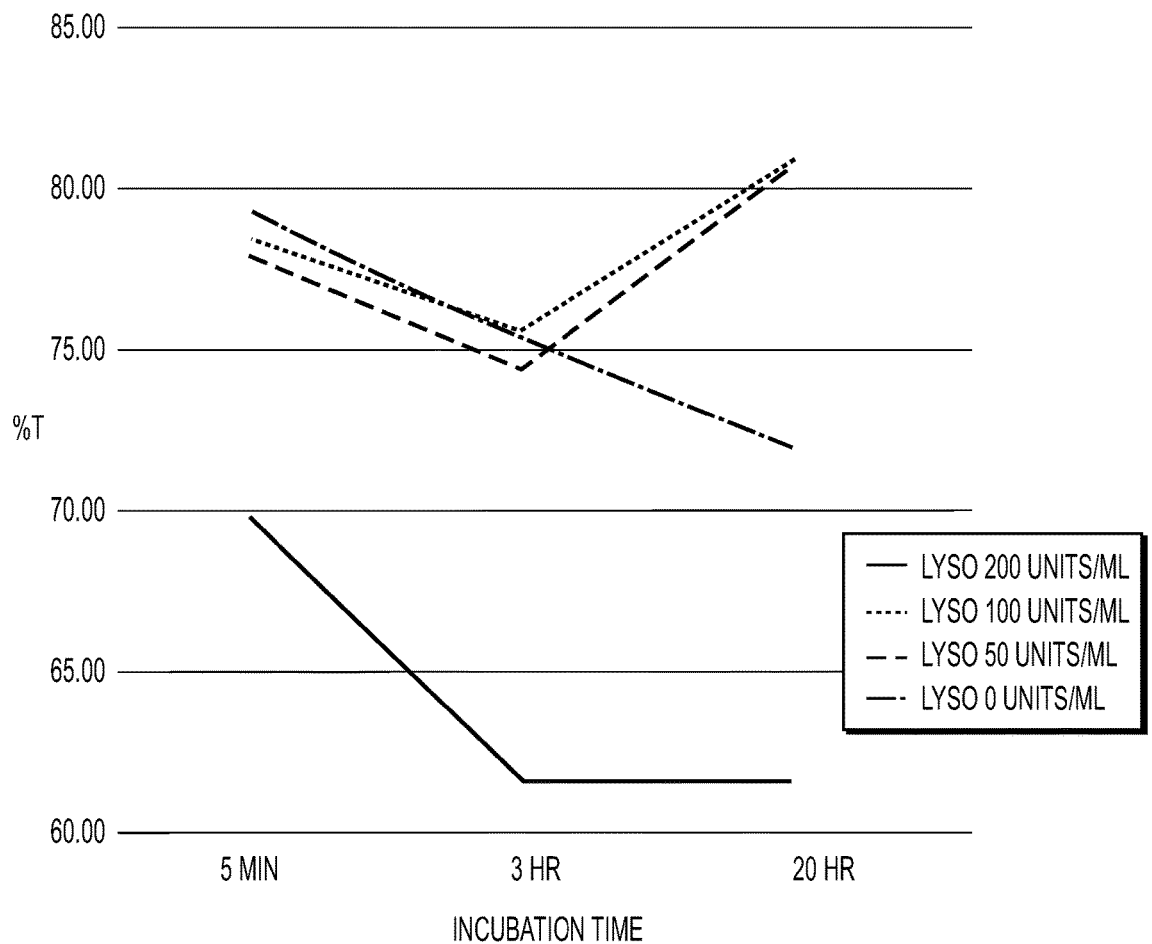
FIG. 4 Effect of Lysostaphin and rifampicin (1 mg/ml) on growth of M. smegmatis.
Figure 5:
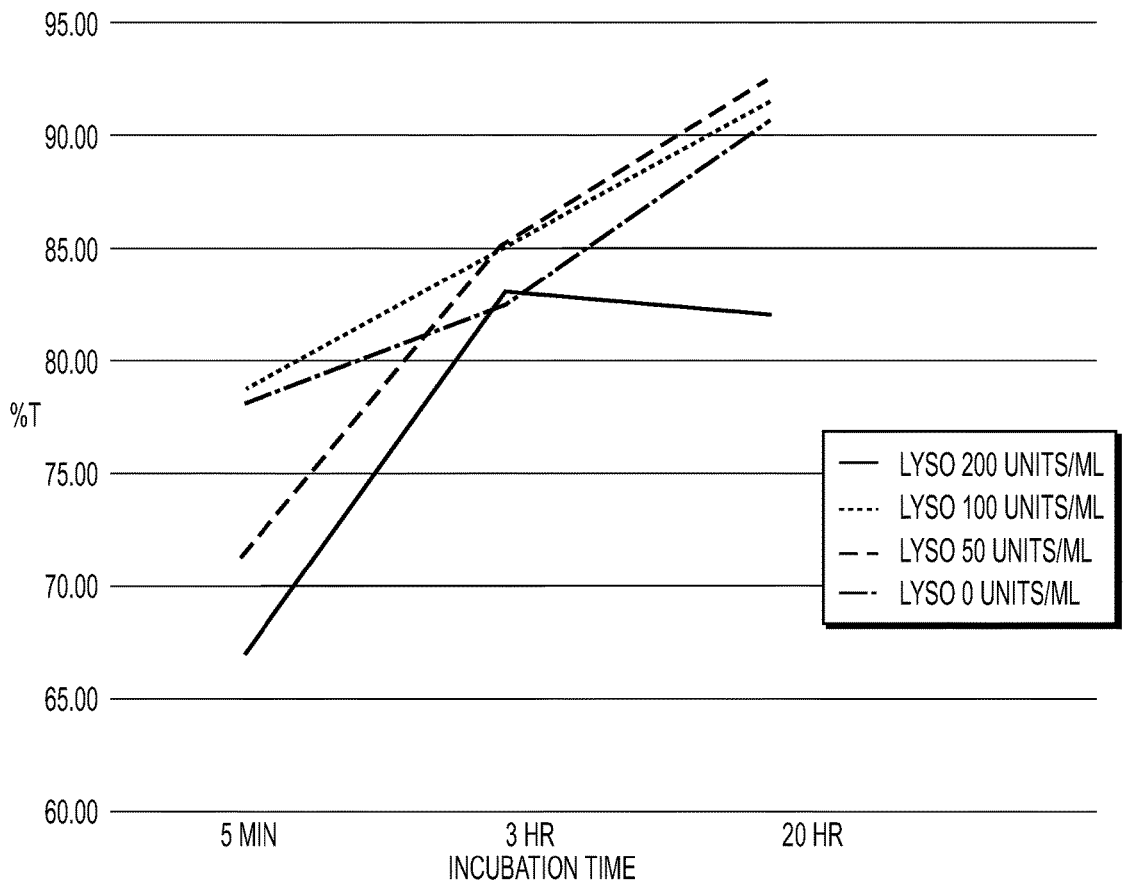
FIG. 5 Effect of Lysostaphin and imipenem (1 mg/ml) on growth of M. smegmatis.

Serum samples were tested using gamma-specific detection (FIGS. 1 and 2). Bars represent binding seen with normal serum (first bar), serum after the first injection (second bar), and serum after the boost injection three weeks later (third and in most cases largest bar). The results on wells coated with simulans lysostaphin (FIG. 1) were stronger than the results on wells coated with *staphylolyticus* lysostaphin (FIG. 2), regardless of the immunogen. Mouse 8621 was poorly reactive on both coating antigens. Note that each graph is scaled to 1.500 on the y-axis for comparison purposes. Based on these results another boost is needed to raise the titers to a level optimal for fusion (i.e. absorbance greater than 1.000 at a serum dilution of 1:10000 or higher).

Example 4

Live *Mycobacterium smegmatis* (MS) Lysostaphin and Antibiotic Data

In this assay, two antibiotics were used at fixed doses—1.0 mg/ml and evaluated mycobacterial lysis/killing with and without lysostaphin (*staphylolyticus* natural lysostaphin) at several concentrations. These data reflect the conditions in serum or tissues where lysostaphin and antibiotics might work in concert to kill or inhibit growth of highly antibiotic resistant bacteria like many mycobacteria. In these studies, *Mycobacterium smegmatis* (MS) was used as a surrogate for *Mycobacterium tuberculosis*. Lysostaphin alone at 200 IU slowed growth a little—% Transmission (% T) with no antibiotic or lysostaphin was minus 45.53 (negative value from baseline equals Growth, while positive equals lysis/killing). Lysostaphin at 200 IU had a minus 31.87% T showing some MS growth inhibition. Imipenem a cell wall active agent at 1.0 mg/ml without lysostaphin lysed/killed MS—% T+12.54, surprisingly with the addition of lysostaphin 50 IU the % T rose to +21.30 and the 50 IU dose was superior to 100 and 200 IU combined with Imipenem. Thus lower levels of cell wall active agents increase synergy and microbial killing. Rifampin alone did not lyse/kill MS—–7.28, with lysostaphin, some lysis/killing did occur (+2.73 at 50 IU and +2.39 at 100 IU). Thus there was synergy using lysostaphin even with Rifampin a polymerase inhibitor to improve MS killing and prevent bacterial growth and again, the highest lysostaphin level was less effective.

Example 5

Effect of Antibiotics and Lysostaphin on Growth of *M. smegmatis*

The *M. smegmatis* was grown on blood agar plate for approximately 48 hours and approximately 75% of the lawn was transferred to 30 mls of H79 Middlebrook broth and grown for approximately three hours at 37° C. with rotation (~250 rpm).

The % T of the *M. smegmatis* suspension was approximately 73.6% at the initiation of the incubation and was reduced to 47.8% at the end of the three hour incubation as determined on the Spec 50. Lysostaphin from *S. staphylolyticus* (Sigma Cat L7386; lot 063M4011V) was prepared at 5 mg/ml (2180 units/nil) in sterile water and further diluted to 200 units/ml in Middlebrook broth. Rifampicin (Sigma Cat R8883) was prepared at 100 mg/ml in DMSO and further diluted in Middlebrook broth to 1 mg/ml. Imipenem monohydrate (Sigma Cat I0160) was prepared at 5 mg/ml in sterile water and further diluted to 1 mg/ml in Middlebrook broth to 1 mg/ml. 50 μl of Lysostaphin at 200, 100 and 50 units/ml were added to the 96-well assay plate in rows A, B and C, respectively. Middlebrook broth (50 μl) was added to the wells in rows D and E.

50 μl of Rifampicin at 1 mg/ml (i.e., 1000 μg/ml) was added to the wells in column 1; 50 μl of a 500 μg/ml solution was added to the wells in column 2 and 50 μl of a 250 μg/ml solution was added to the wells in column 3. As the 1000 μg/ml solution was in a solution containing 1% DMSO, the wells in column 4 contained 50 μl of 1% DMSO in Middlebrook broth. Similarly, 50 μl of 1000, 500 and 250 μg/ml solutions of Imipenem monohydrate were added to columns 5, 6 and 7. Fifty μl of Middlebrook broth alone was added to the wells in column 8. 150 μl of *M. smegmatis* (~47.8% T as determined in the Spec 50) was added to all wells in rows A-D. 150 μl of Middlebrook broth only was added to wells in row E and also to well F8. Wells E8 and F8 served as the blank wells for the % T readings in the 96-well plate reader. The plate was read (650 nm) after approximately 5 minutes. The plate was then incubated for three hours at 37° C. with gentle rotation (50 rpm). Another reading was made and the plate was incubated overnight and a final reading was made.

TABLE 3

Results with Lysostaphin Alone

| Lysostaphin | % T | | |
|---|---|---|---|
| (units/ml) | 5 min | 3 hours | 20 hours |
| 200 | 77.34 | 71.54 | 45.47 |
| 0 | 80.11 | 70.79 | 34.58 |

Table 3 and FIG. 3 show the results obtained with Lysostaphin alone. Only the data from 200 units/ml and 0 units/ml are shown, as the results with all levels of Lysostaphin were essentially the same (327 units/mg {1 IU=3.1 μg}). The data show that while there was little change in the % T through 3 hours, the % T decreased nearly the same amount with or without Lysostaphin following overnight incubation.

TABLE 4

Results with Rif (1 mg/ml) and Lysostaphin

| Lysostaphin | % T | | |
|---|---|---|---|
| (units/ml) | 5 min | 3 hours | 20 hours |
| 200 | 69.69 | 61.55 | 61.47 |
| 100 | 78.47 | 75.57 | 80.86 |
| 50 | 77.89 | 74.53 | 80.62 |
| 0 | 79.25 | 75.27 | 71.79 |

Table 4 and FIG. 4 show the results with a titration of Lysostaphin and Rifampicin at 1 mg/ml. The % T increased between the 3 hour and 20 hour reading with Lysostaphin at 100 and 50 units/ml, while with no Lysostaphin the % T decreased. However, the % T also decreased with Lysostaphin at 200 units/ml. The changes in % T were quite narrow. The % T also increased with Imipenem (FIG. 5) with all doses of Lysostaphin, except at 200 units/ml where the % T reached a plateau. Without Lysostaphin the % T also increased. As with Rifampicin, the range of the % T was not large.

TABLE 5

Results with Imp (1 mg/ml) and Lysostaphin

| Lysostaphin | % T | | |
|---|---|---|---|
| (units/ml) | 5 min | 3 hours | 20 hours |
| 200 | 66.83 | 82.92 | 82.06 |
| 100 | 78.61 | 85.10 | 91.49 |
| 50 | 71.17 | 85.20 | 92.42 |
| 0 | 78.00 | 82.67 | 90.54 |

Table 5 and FIG. 5 show that Lysostaphin treatment alone did not result in an increase in the % T over the 20 hours of the experiment. In fact, the % T decreased, indicating growth of the bacteria. When Rifampicin (1 mg/ml) was included, the % T increased with 100 and 50 units/ml, while without Lysostaphin (i.e. Rifampicin alone) the % T decreased. These results show a synergistic effect between the Lysostaphin and Rifampicin. With Imipenem, the % T increased over time, with and without Lysostaphin. With both antibiotics the results with 200 units/ml of Lysostaphin either showed a decrease in % T or the % T reached a plateau.

In the studies shown in Tables 3-5 (also depicted in FIGS. 3-5), two antibiotics were used at fixed doses—1.0 mg/ml and evaluated mycobacterial lysis/killing with and without lysostaphin at several concentrations. These data reflect the conditions in serum or tissues where lysostaphin and antibiotics might work in concert to kill or inhibit growth of highly antibiotic resistant bacteria like many mycobacteria. In these studies, MS was used as a surrogate for *Mycobacterium tuberculosis*. Lysostaphin alone at 200 IU slowed growth a little- % Transmission (% T) with no antibiotic or lysostaphin was −45.53 (negative value from baseline equals Growth, while positive equals lysis/killing). Lysostaphin at 200 IU had a −31.87% T showing some MS growth inhibition. Imipenem a cell wall active agent at 1.0 mg/ml without lysostaphin lysed/killed MS—% T+12.54, surprisingly with the addition of lysostaphin 50 IU the % T rose to +21.30 and the 50 IU dose was superior to 100 and 200 IU combined with Imipenem. Thus lower levels of cell wall active agents increase synergy and microbial killing. Rifampin alone did not lyse/kill MS—−7.28, with lysostaphin, some lysis/killing did occur (+2.73 at 50 IU and +2.39 at 100 IU). Thus there was synergy using lysostaphin even with Rifampin a polymerase inhibitor to improve MS killing and prevent bacterial growth and again, the highest lysostaphin level was less effective.

Other embodiments and uses of the invention will be apparent to those skilled in the art from consideration of the specification and practice of the invention disclosed herein. All references cited herein, including all publications, U.S. and foreign patents and patent applications, and U.S. Application entitled "Ultra-Low Dose Lysostaphin for Treating MRSA" filed contemporaneously herewith, are specifically and entirely incorporated by reference. The term comprising, where ever used, is intended to include the terms consisting and consisting essentially of. Furthermore, the terms comprising, including, containing and the like are not intended to be limiting. It is intended that the specification and examples be considered exemplary only with the true scope and spirit of the invention indicated by the following claims.

The invention claimed is:

1. A method for treating an infection caused by Mycobacterial organisms comprising administering to a patient in need thereof a pharmaceutical composition consisting of lysostaphin at from 5 pg to 0.5 mg of lysostaphin/kg of patient weight.

2. The method of claim 1, wherein the effective amount of lysostaphin is administered in one or more doses.

3. The method of claim 1, wherein the effective amount of lysostaphin is administered in one or more doses and provides a serum or tissue level of lysostaphin at from 0.001 pg/ml to 50 pg/ml.

4. The method of claim 1, wherein the effective amount of lysostaphin is administered in one or more doses and provides a serum or tissue level of lysostaphin at from 0.01 pg/ml to 20 pg/ml.

5. The method of claim 1, wherein the composition is encapsulated with a biodegradable polymer that provides for slow-release or timed-release of the lysostaphin.

6. The method of claim 1, wherein the lysostaphin is aerosolized to an average particle size of about 1-3 microns or less.

7. The method of claim 1, wherein the lysostaphin is aerosolized as nanoparticles.

8. The method of claim 7, wherein the nanoparticles are administered to the lungs.

9. The method of claim 1, wherein the composition is coated onto an object to be inserted into the body of the patient.

10. The method of claim 9, wherein the object is inserted into an area of the body of the patient that is sequestered from the patient's immune system.

11. The method of claim 1, wherein the composition has reduced negative effects or increased positive effects for the patient as compared with conventional therapy.

12. The method of claim 11, wherein the reduced negative effects include one or more of reduced toxicity and reduced immunogenicity, and the increased positive effects include one or more of increased efficacy and enhanced clearance of a non-Staphylococcal organism.

13. The method of claim 1, wherein the lysostaphin is wild-type or recombinant lysostaphin.

14. The method of claim 13 wherein the recombinant lysostaphin is isolated from a culture of cells other than *Staphylococcus* cells.

15. The method of claim 14, wherein the culture of cells other than the *Staphylococcus* cells is *E. coli* cells.

16. The method of claim 13, wherein the recombinant lysostaphin has one or more amino acids or one or more amino acid modifications that differ from wild-type lysostaphin.

17. The method of claim 13, wherein the recombinant lysostaphin has a greater efficacy against a non-*Staphylococcus* infection as compared to wild-type lysostaphin.

18. The method of claim 13, wherein recombinant lysostaphin has a reduced or no immune response when administered to the patients in need thereof as compared to wild-type lysostaphin.

19. The method of claim 13, further comprising a secondary therapy for the patient in need thereof that is synergistic with the lysostaphin.

20. The method of claim 19, wherein the secondary therapy comprises administration of chemical compounds, antimicrobials, bacteriocins, antibodies and/or antibiotics.

21. The method of claim 20, wherein the secondary therapy comprises an agent that has activity against cell walls.

22. The method of claim 20, wherein the lysostaphin is administered at a dose that does not initially kill or destroy all non-Staphylococcal organisms.

23. The method of claim 1, wherein the effective amount of lysostaphin is administered in one or more doses of 10 pg per kg of patient body weight.

24. The method of claim 1, wherein the effective amount of lysostaphin is administered in one or more doses of 50 pg per kg of patient body weight.

25. The method of claim 1, wherein the effective amount of lysostaphin is administered in one or more doses of 100 pg per kg of patient body weight.

26. The method of claim 1, wherein the Mycobacterial organisms comprise *M. sinegiatis* and/or *M. tuberculosis*.

* * * * *